United States Patent [19]
Mollenauer et al.

[11] Patent Number: 5,730,731
[45] Date of Patent: Mar. 24, 1998

[54] PRESSURE-BASED IRRIGATION ACCUMULATOR

[75] Inventors: Kenneth H. Mollenauer, Santa Clara; Albert K. Chin, Palo Alto; Hee Jung K. Wescoat, Garden Grove, all of Calif.

[73] Assignee: Thomas J. Fogarty, Palo Alto, Calif.

[21] Appl. No.: 677,246

[22] Filed: Jul. 9, 1996

Related U.S. Application Data

[63] Continuation of Ser. No. 653,652, Feb. 11, 1991, abandoned, which is a continuation-in-part of Ser. No. 328,760, Mar. 23, 1989, Pat. No. 4,998,972, which is a continuation of Ser. No. 187,591, Apr. 28, 1988, abandoned.

[51] Int. Cl.$^6$ ................................................. A61M 1/00
[52] U.S. Cl. ................................................................ 604/246
[58] Field of Search .................. 128/DIG. 12, DIG. 13; 604/65–67, 246–249, 30–34, 49–53, 27

[56] References Cited

U.S. PATENT DOCUMENTS

| | | | |
|---|---|---|---|
| 3,731,679 | 5/1973 | Wilhelmson et al. | 128/DIG. 13 |
| 3,799,702 | 3/1974 | Weishaar | 128/DIG. 12 |
| 4,117,843 | 10/1978 | Banko | 604/65 |
| 4,207,871 | 6/1980 | Jenkins | 604/65 |
| 4,210,138 | 7/1980 | Jess et al. | 128/DIG. 13 |
| 4,432,468 | 2/1984 | Siff et al. | 604/65 |
| 4,534,756 | 8/1985 | Nelson | 604/65 |
| 4,586,920 | 5/1986 | Peabody | 604/65 |
| 4,613,325 | 9/1986 | Abrams | 128/DIG. 13 |
| 4,613,327 | 9/1986 | Tagarian et al. | 128/DIG. 12 |
| 4,778,451 | 10/1988 | Kamen | 128/DIG. 13 |
| 4,940,457 | 7/1990 | Olson | 604/247 |
| 4,998,914 | 3/1991 | Wiest et al. | 128/DIG. 13 |
| 5,207,642 | 5/1993 | Orkin et al. | 604/65 |

*Primary Examiner*—Manuel Mendez
*Attorney, Agent, or Firm*—Limbach & Limbach L.L.P.

[57] ABSTRACT

A pressure-based irrigation accumulator system utilizable in an angioscopy imaging system includes reservoir means for storing irrigation solution under pressure, pressure means for pressurizing the reservoir means to a preset pressure limit, and delivery means for delivering irrigation solution from the reservoir means to a destination.

6 Claims, 9 Drawing Sheets

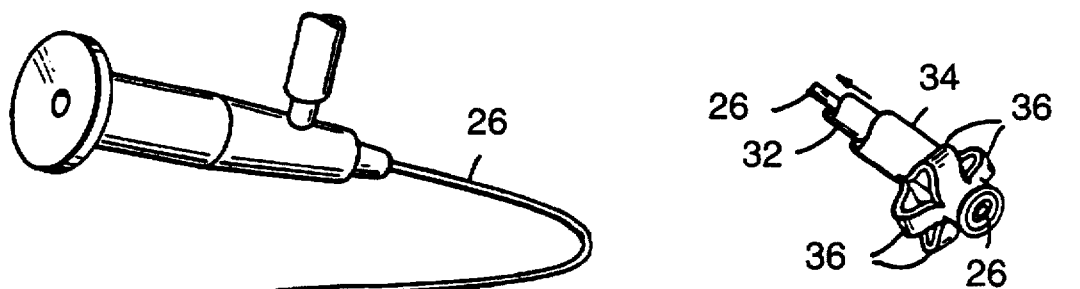
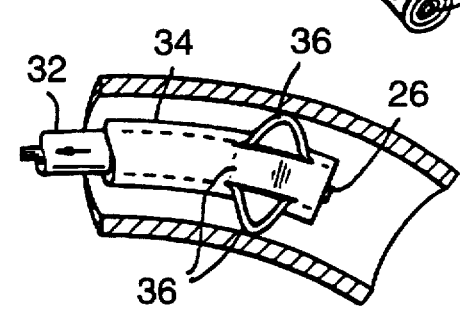
FIG. 4B
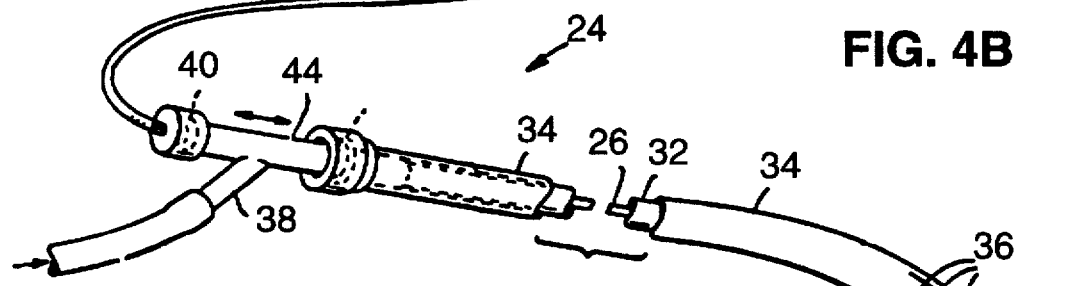
FIG. 4A
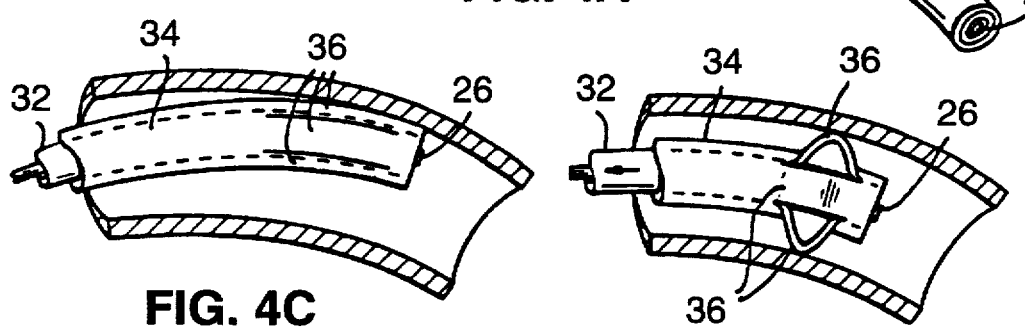
FIG. 4C
FIG. 4D
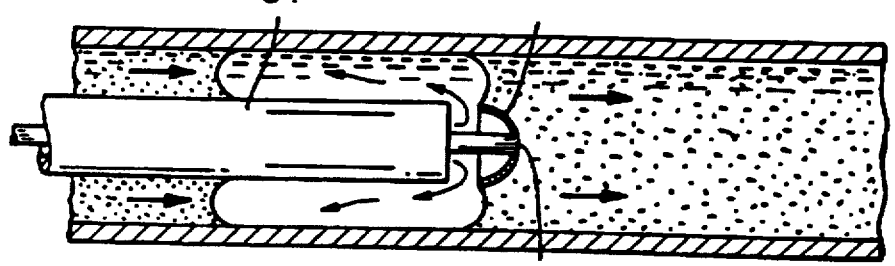
FIG. 8A
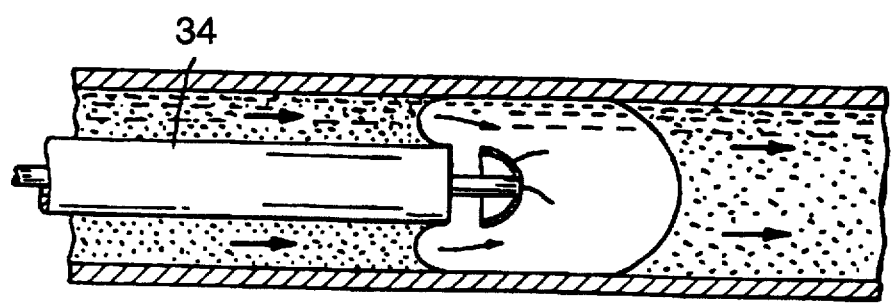
FIG. 8B

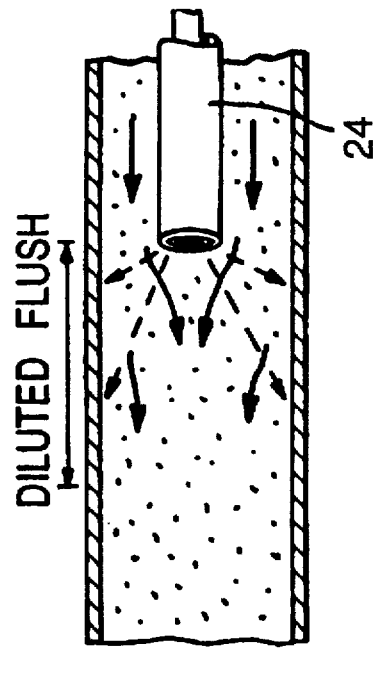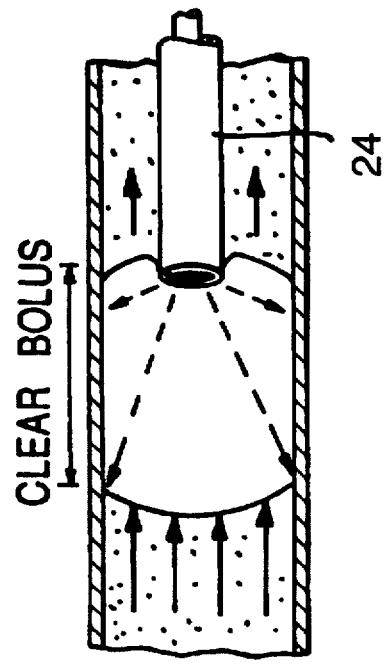
FIG. 6A
FIG. 6B
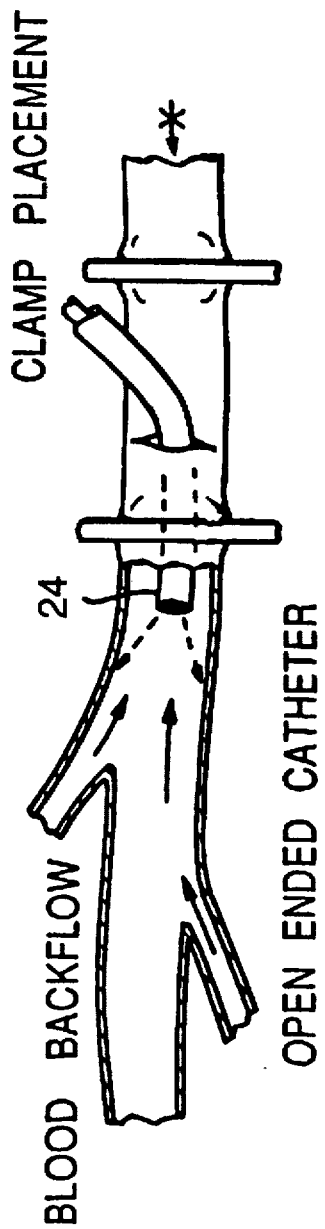
FIG. 7

2

PRESSURE-BASED IRRIGATION ACCUMULATOR

RELATED APPLICATION

This is a continuation of application Ser. No. 07/653,652 filed on Feb. 11, 1991 now abandoned which is a continuation-in-part of U.S. patent application Ser. No. 328,760, filed Mar. 23, 1989 (now U.S. Pat. No. 4,998,972), which is a continuation of U.S. patent application Ser. No. 187,591, filed Apr. 28, 1988 by Albert K. Chin et al for REAL TIME ANGIOSCOPY IMAGING SYSTEM and now abandoned.

BACKGROUND OF THE INVENTION

1. Field of the Invention

The present invention relates generally to fluid delivery systems and, in particular, to a pressure-based irrigation accumulator utilizable for providing pulsatile irrigation in an angioscopy imaging system.

2. Discussion of the Prior Art

It is well-known that optical scopes may be used for direct visualization of body passages. For example, endoscopes are used for viewing the gastrointestinal tract, bronchoscopes are used for viewing bronchial passages, and arthroscopes are used for joint examination. These scopes are moved to a position within the body that the viewer desires to examine. The body passage is then visualized directly through the eyepiece of the scope or through a video camera attached to the scope to display the image on a video monitor.

An angioscope is used for viewing both the arterial and the venous systems. In the angioscopy procedure, a fiberoptic scope is inserted into the vessel through an incision or puncture and then threaded through the vessel to provide visualization at selected points along the length of the vessel. Sterile saline flush solution is introduced continuously into the vessel to provide a clear visualization field.

Angioscopy is particularly difficult in the arterial system. The pressure and the flow rate of the blood are much higher in the arteries than in the veins, making it difficult to obtain the clear, bloodless field required for the desired quality of visualization. If only a small amount of saline is used to flush away the blood, then this irrigation solution is washed away too quickly to allow adequate visualization. On the other hand, if a larger amount of irrigation solution is used, over a time period sufficient to allow adequate visualization, complications will arise. First, fluid overload of the patient will occur, causing electrolyte imbalance or congestive heart failure. Second, there will be a lack of perfusion to the tissue supplied by the artery undergoing angioscopy because the flush fluid has cleared away the oxygen-carrying blood. This problem is particularly difficult in angioscopic evaluation of the coronary arteries, since the cardiac muscle cannot tolerate prolonged ischemia. Balloon occlusion may be used, but it too may cause ischemia.

Existing angioscope irrigation systems are typically roller pump, volume flow-based systems. The pressures delivered to the angioscope catheter in a flow-based system are dependent upon the pump flow rate and flow restrictions downstream of the pump. In an open ended system (e.g. in an unclamped vessel), a relatively constant pressure is reached after the pump comes up to speed and the system reaches its predetermined steady flow rate. However, currently-designed roller pumps will attempt to deliver irrigation solution at their preset flow rate without regard to the pressure in the vascular system. Thus, in a closed system (e.g. a distally clamped or occluded vessel), pressure will increase to a point where either the pump bypasses at a high pressure or the system fails, i.e. the vessel ruptures.

Therefore, it would be highly desirable to have available an irrigation system that provides clear angioscopy visualization within the irrigation constraints described above.

SUMMARY OF THE INVENTION

The present invention provides a pressure-based irrigation accumulator system utilizable for angioscopy. Two embodiments are disclosed: a reservoir system and a roller pump based system.

A reservoir irrigation system in accordance with the present invention includes a saline reservoir contained in a gas-over-saline or water-over-saline pressure vessel, a pressure regulator for setting, adjusting and maintaining pressure on the saline reservoir, and a hand or foot operated actuating valve for controlling the flow of irrigation solution from the saline reservoir to an angioscopy system.

A roller pump based irrigation system in accordance with the present invention utilizes a constant-pressure roller pump to deliver saline solution from a saline reservoir to a hypodermic syringe equipped with a metal spring or an air spring to hold fluid under pressure. A switching mechanism in the syringe system senses when the saline pressure within the syringe is at or below a preset limit and turns the roller pump off and on accordingly, thus constantly attempting to maintain the pressure within the syringe at the preset limit. As with the reservoir system, a hand or foot operated actuating valve controls the flow of irrigation solution from the syringe to the angioscopy system. As soon as the syringe has delivered a pulse of irrigation solution, the switching mechanism turns the roller pump on to refill the syringe to the preset pressure.

Both the reservoir and the roller pump irrigation accumulator designs provide advantages over conventional angioscopy irrigation systems. First, the human vessel cannot be inadvertently overpressurized. Second, both systems provide instant pressure with instant flow for instant observation through the angioscope. This feature makes angioscopy more user-friendly and also allows for reduced infusion of saline into the patient. Third, the sharply pulsatile irrigation provided by both systems makes it easier to identify intimal flaps, blood effusing from side-branches and the location of valve sites.

A better understanding of these and other features and advantages of the present invention will be obtained by reference to the following detailed description of the invention and accompanying drawings which set forth illustrative embodiments in which the principles of the invention are utilized.

BRIEF DESCRIPTION OF THE DRAWINGS

FIG. 4A is a pictorial view illustrating an angioscope centering catheter.

FIG. 4B is a pictorial view illustrating the distal end of the angioscope centering catheter shown in FIG. 4A after splaying of the longitudinal slitted sections.

FIG. 4C is a cross-sectional view illustrating the catheter shown in FIG. 4A in a curved section of vessel prior to centering.

FIG. 4D is a cross-sectional view illustrating the catheter shown in FIG. 4A in a curved section of vessel after centering.

FIG. 6A is a cross-sectional view illustrating the use of a catheter for saline irrigation against blood flow.

FIG. 6B is a cross-sectional view illustrating the use of a catheter for saline irrigation with blood flow.

FIG. 7 is a cross-sectional view illustrating intraoperative angioscopy.

FIG. 8A and 8B are cross-sectional view illustrating introduction of irrigation solution utilizing a deflector shield.

DETAILED DESCRIPTION OF THE INVENTION

Figure 1:
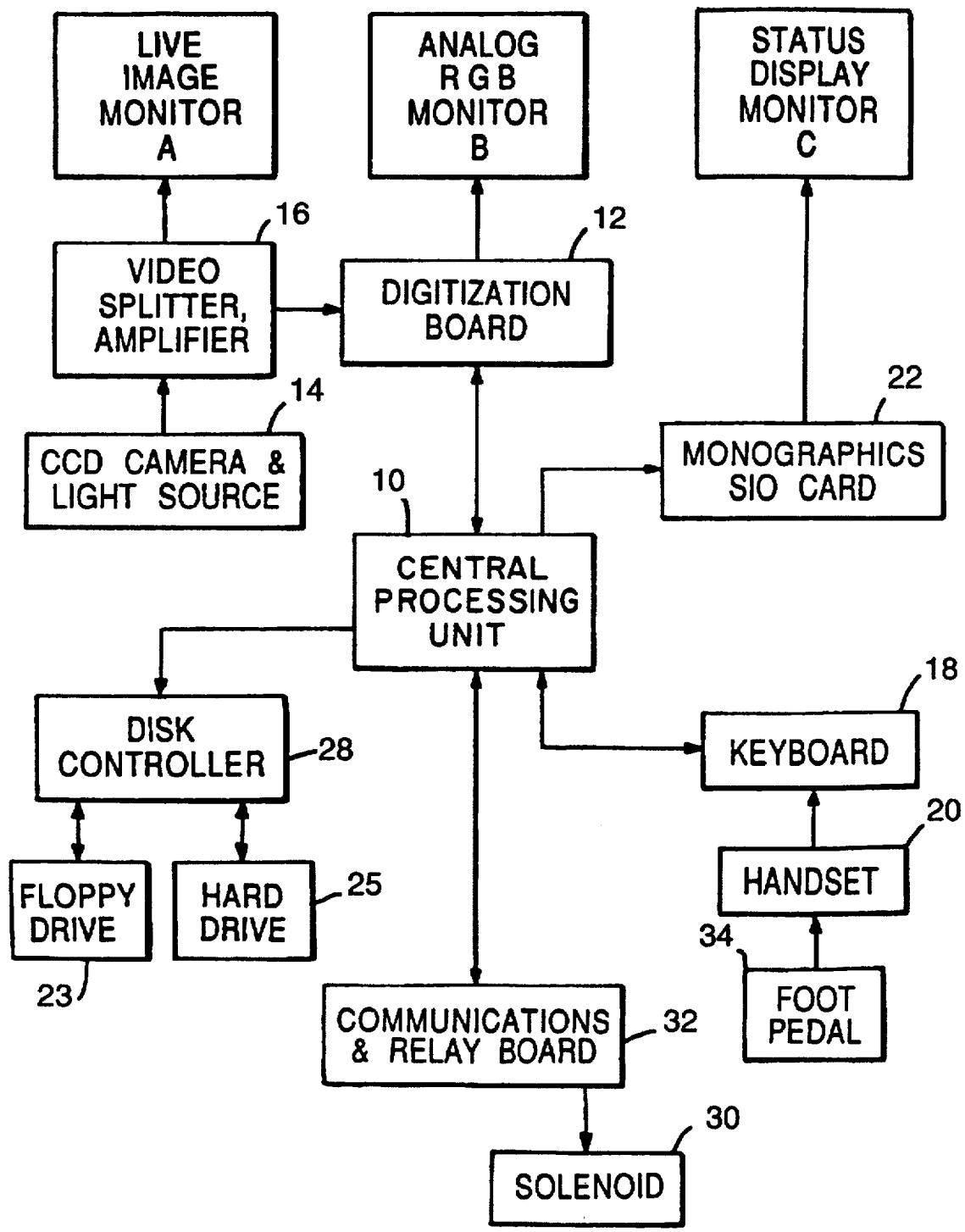
FIG. 1 is a block diagram illustrating the general concept of an automated angioscopy imaging system.
Figure 2:
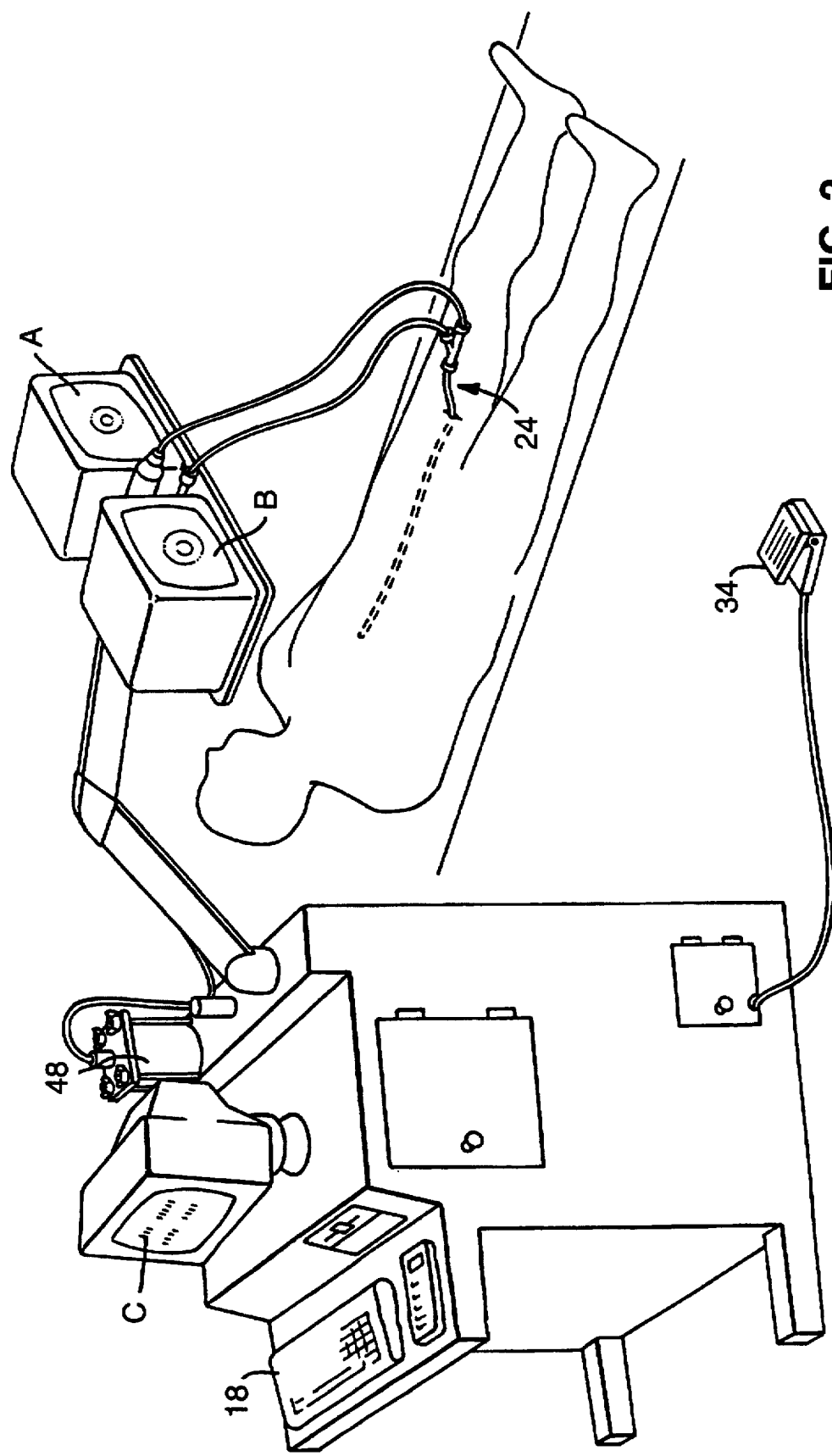
FIG. 2 is a pictorial illustration of the FIG. 1 angioscopy imaging system in an operating room environment.
Figure 3:
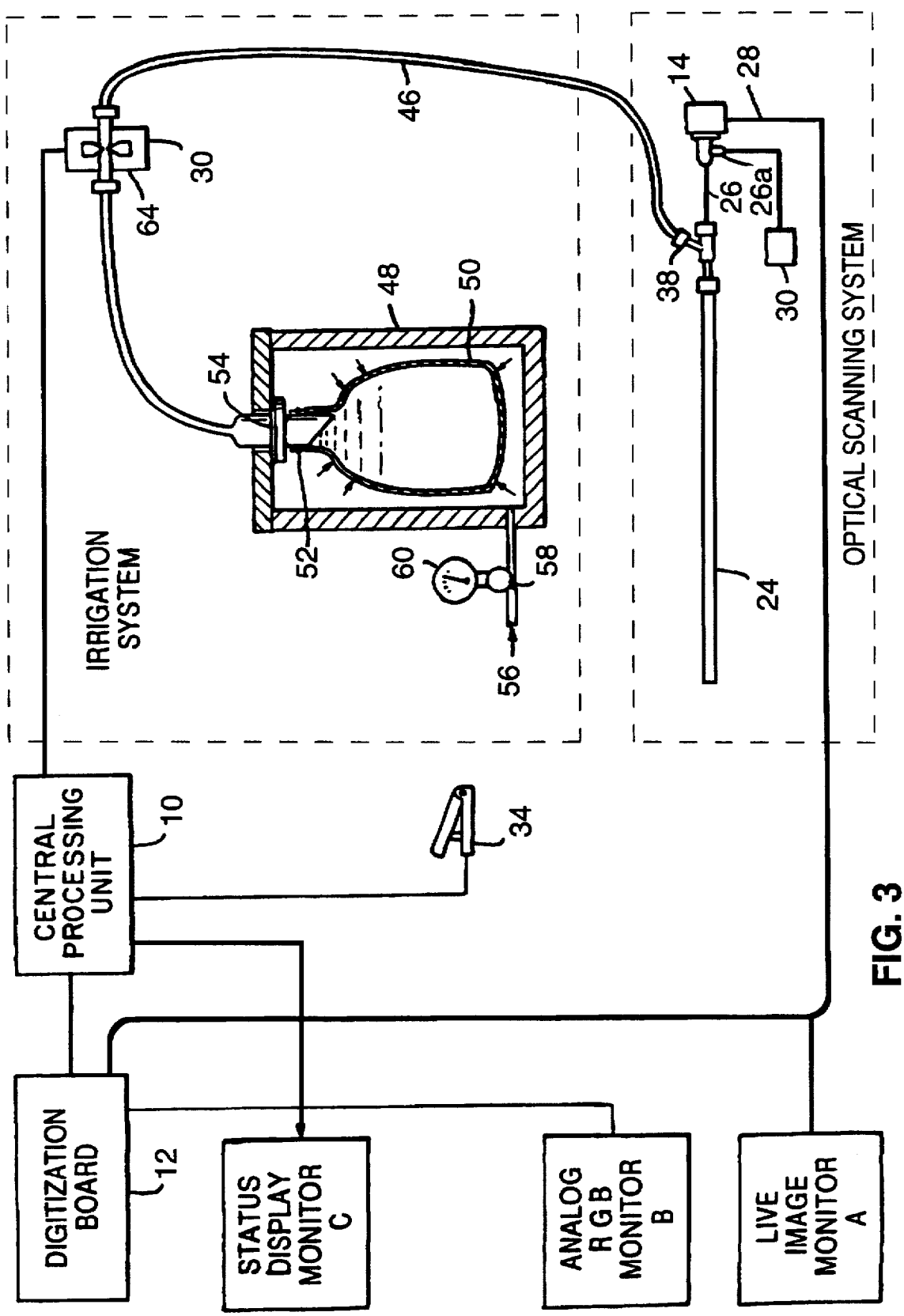
FIG. 3 is a schematic diagram illustrating an angioscope catheter and an embodiment of an irrigation accumulator system in accordance with the present invention.

An angioscopy imaging system in which a pressure-based irrigation accumulator system in accordance with the present invention may be utilized is illustrated in FIGS. 1–3, wherein like reference numerals specify like elements.

FIG. 1 shows a block diagram of such an angioscopy imaging system. The illustrated system operates under the control of a computer system which includes imaging control and irrigation control hardware. The imaging control hardware controls an optical scanning system which is inserted into the interior of a vessel for generation of a digitized image. The irrigation control hardware controls a pressure-based irrigation accumulator system, to be described in detail below, which, in accordance with the present invention, provides pulsed introduction of irrigation solution into the interior of a vessel (e.g. an artery) to create a clear viewing field within the vessel for the optical scanning system. The computer system controls both the optical scanning system and the irrigation accumulator system such that the generation of the digitized image is synchronized with the pulsed introduction of the irrigation solution.

The system shown in FIG. 1 operates under the control of a central processing unit 10. The central processing unit 10 communicates with a digitization board 12 which generates a digitized image signal that corresponds to a live image captured by camera and light source 14. The live image signal generated by camera/light source 14 is provided to the digitization board 12 via a video splitter/amplifier 16 which also provides the live image signal to monitor A for direct display. The digitization board 12 provides the digitized image signal to monitor B for display of a digital image. Status information, which can be entered either via a keyboard 18 or a handset 20, is displayed on a status display monitor C via monographic serial input/output card 22. CPU 10 can access both floppy drive storage 23 and hard drive storage 25 via a disk controller 28. Pulses of pressurized saline irrigation solution are provided to an angioscope catheter on command from the central processing unit 10 which opens and closes a solenoid valve 30 via communications and relay board 32.

A pictorial illustration of the above-described angioscopy imaging system in an operating room environment is provided in FIG. 2.

Referring to FIG. 3, the optical scanning system includes an angioscope catheter 24 which houses an angioscope 26 which is attached to the video camera and light source 14. As stated above, the output signal of the video camera, designated "28" in FIG. 3, is provided both to a live monitor A and to the digitization board 12 for digitization and viewing on monitor B in real time. The light source, designated "30" in FIG. 3, attaches to the eyepiece 26a of the angioscope 26.

Referring to FIGS. 4A–4D, the angioscope catheter 24 comprises an inner catheter 32 which slides longitudinally with respect to an outer sheath 34. The outer sheath 34 includes a plurality of slitted sections 36 formed circumferentially near its distal end. The outer sheath 34 is bonded to the inner catheter 32 at their distal-most points. Thus, when the inner catheter 32 is pulled proximally with the outer sheath 34 held fixed, the slitted sections 36 of the outer sheath 34 splay out radially from the axis of the catheter 32 in a symmetrical fashion. This centers the angioscope during visualization, particularly in curved sections of the vessel, as best shown in FIGS. 4C and 4D. At the same time, it allows blood to flow in the vessel during the angioscopy procedure.

The angioscope 26 comprises an illuminated fiberoptic scope which extends through the inner catheter 32 for viewing through the open distal end of the catheter 32. The fiberoptic scope 26 may be of the lighted type manufactured by Baxter, Edwards LIS Division, Santa Ana, Calif. Such scopes have central viewing strands which are surrounded by peripheral illuminating strands. Although not illustrated in FIGS. 4A–4D, it should be understood that the proximal end of the scope 26 would be secured to the video camera and light source 14, as shown in FIG. 3.

As further shown in FIG. 4A, the angioscope centering catheter 24 also includes an irrigation port 38 for pulsatile irrigation of the vessel through the inner catheter 32. The angioscope 26 is held in place within the inner catheter 32 by means of an O-ring seal 40. A second 0-ring seal 42 prevent blood from seeping out between the inner catheter 32 and the outer sheath 34. This second O-ring seal 42 slides longitudinally along a rigid section 44 that houses the inner catheter 32 to provide the splaying of the slitted sections 36 as described above. The rigid section 44 permits easy movement of the outer sheath and the inner catheter with respect to one another. The angioscope centering catheter 24 is described in detail in U.S. Pat. No. 4,878,893, issued Nov. 7, 1989, to Dr. Albert K. Chin. U.S. Pat. No. 4,878,893, which is commonly-assigned herewith to Dr. Thomas J. Fogarty, is hereby incorporated by reference. Referring back to FIG. 3, the angioscope centering catheter 24 is irrigated with sterile saline via the irrigation port 38 by means of an irrigation line 46 connected to a pressure vessel 48. The pressure vessel 48 houses a bag 50 of sterile saline which is attached to the irrigation line 46 by means of an irrigation line spike 52. An O-ring 54 seals the irrigation line spike 52 against the cover of the pressure vessel 48. Compressed air is supplied to the pressure vessel 48 via an air pressure inlet 56. The pressure within the vessel 48 is adjusted by a regulator 58 and is measured by pressure gauge 60.

As stated above, pulses of pressurized saline irrigation solution are delivered to the irrigation port 38 on command from the computer system, which opens and closes a solenoid pinch valve 30. The solenoid pinch valve 30 pinches a section of silicone tubing 64 which lies in line with the irrigation line 46. Alternatively, the solenoid pinch valve can be replaced by a hand or foot operated actuating valve for direct manual control of the flow of irrigation solution from the saline reservoir to the catheter 24.

The computer system may be programmed to deliver a sequence of timed irrigation pulses or a single pulse may be delivered by means of the foot pedal switch 34 connected to the central processing unit 10 via communications and relay board 32.

A saline irrigation pulse is activated for a duration of approximately one second, the duration of the pulse being dependent upon the patient, the size of the vessel and the type of catheter used. The clear analog image of the interior of the vessel which is captured by the camera during irrigation is digitized and displayed on monitor B and the image is frozen until the next flush cycle.

A stable monitor image is desired, with no black screen or interrupted images between monitor picture changes. This requires storage of the incoming image from the angioscope 34. Therefore, the analog image signal generated by the video camera 28 is digitized, stored in memory of the computer system and projected on video monitor B. The image is refreshed continuously, preferably at a rate of at least 30 times per second, until the image is changed with the next flush cycle, as illustrated in FIGS. 5A-D; the eye can perceive no black screen or interruption of the image at this speed of image refreshing.

As stated above, it is difficult to obtain a bloodless viewing field in the arteries because of the higher pressure and flow rate of blood in these vessels. Therefore, as shown in FIG. 6, it is preferred that the angioscope 24 be inserted in the vessel such that saline irrigation is directed against the direction of blood flow to create a bolus of saline irrigation solution that is visually clear for the focal distance of the angioscope 24. For the fiber optic scope identified above, this distance is approximately 15 mm. Irrigation is directed against the blood flow to achieve clearing with the minimal amount of saline. Experiments have shown that the irrigation stream is diluted if irrigation is in the direction of blood flow, as shown in FIG. 6A, and clearing is only obtained with large volumes of irrigation solution. On the other hand, irrigation against the blood flow establishes a clear area where opposing fronts of irrigation solution and blood flow meet.

The catheter design used to irrigate against blood flow will vary with the situation and application. For intraoperative angioscopy, the artery will be isolated in the operating room, and an arteriotomy made to admit the angioscope. As shown in FIG. 7, the artery will be clamped proximal and distal to the arteriotomy site. If the angioscope 24 is advanced in a distal direction, there is no forward blood flow, only backflow from collateral side branches. Thus, the irrigation catheter may be a straight, open ended catheter. If the angioscope is advanced in a proximal direction, it is again going against blood flow and a straight, open ended catheter will again be appropriate.

For percutaneous angioscopy, the angioscope is introduced via a needle puncture and an introducing sheath into the artery. Usually, the access site is the femoral artery. If the angioscope is threaded distally, it lies in the same direction as the blood flow. The catheter must now irrigate backwards to form a bolus which going against the blood flow. As shown in FIGS. 8A and 8B, such a catheter may include a port which allows the irrigation solution to hit a deflecting shield at the distal tip of the angioscope, thus causing the irrigation solution to stream backwards. (A catheter that implements this type of deflector is disclosed in the above-referenced Chin et al patent.) If the angioscope is threaded proximally, a straight, open ended catheter will be used.

The timing of the irrigation is important. In the peripheral arteries, the blood flow may come to a standstill or even reverse its direction of flow in diastole. On the other hand, in the coronary arteries, forward blood flow occurs during diastole. The irrigation may be timed with the cardiac cycle of systole and diastole by triggering the irrigation with an electrocardiogram. An electrode pickup may be input to the computer to control the irrigation cycle.

Figure 5I:
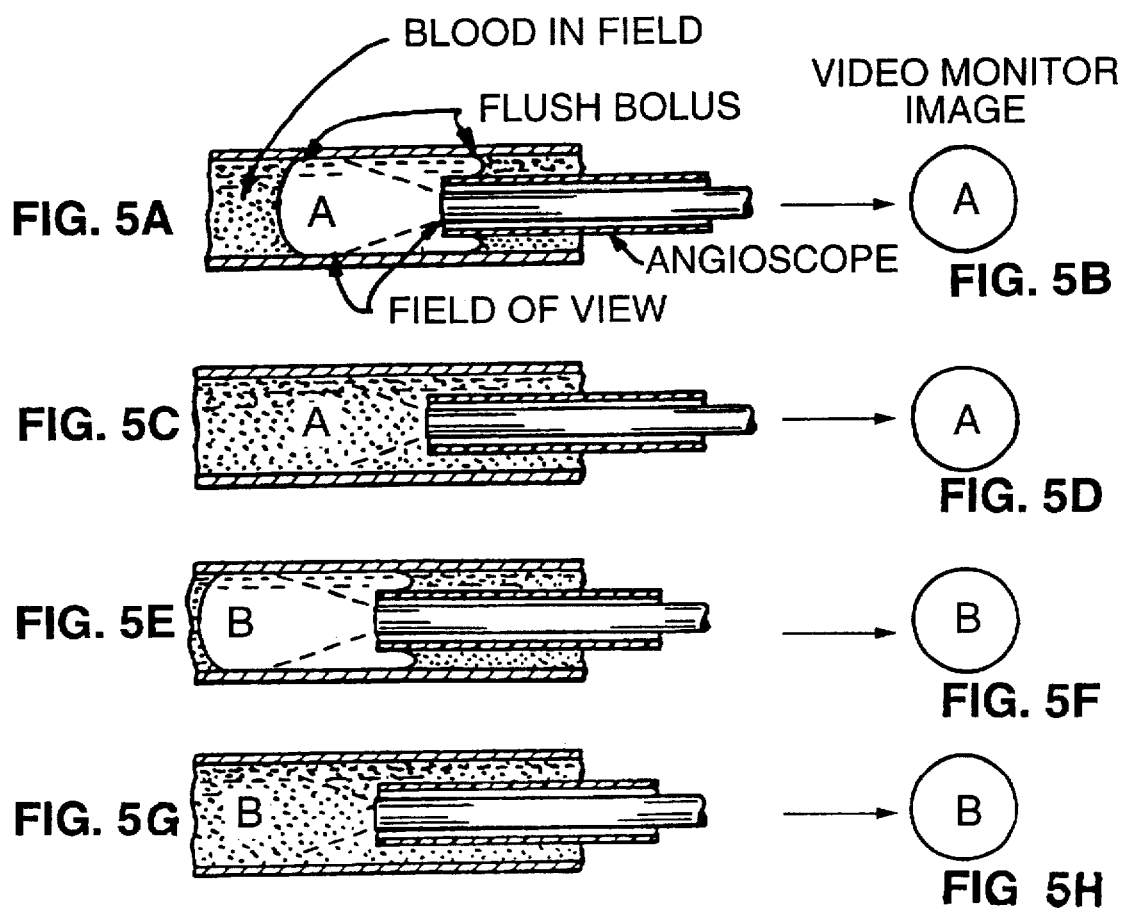
FIGS. 5A–5D provide a series of schematic drawings illustrating a synchronized flush/imaging sequence utilizing an irrigation accumulator system in accordance with the present invention.
FIGS. 5E–F are timing diagrams illustrating an automatic synchronized irrigation/imaging sequence utilizing an irrigation accumulator system in accordance with the present invention.
Figure 5I:
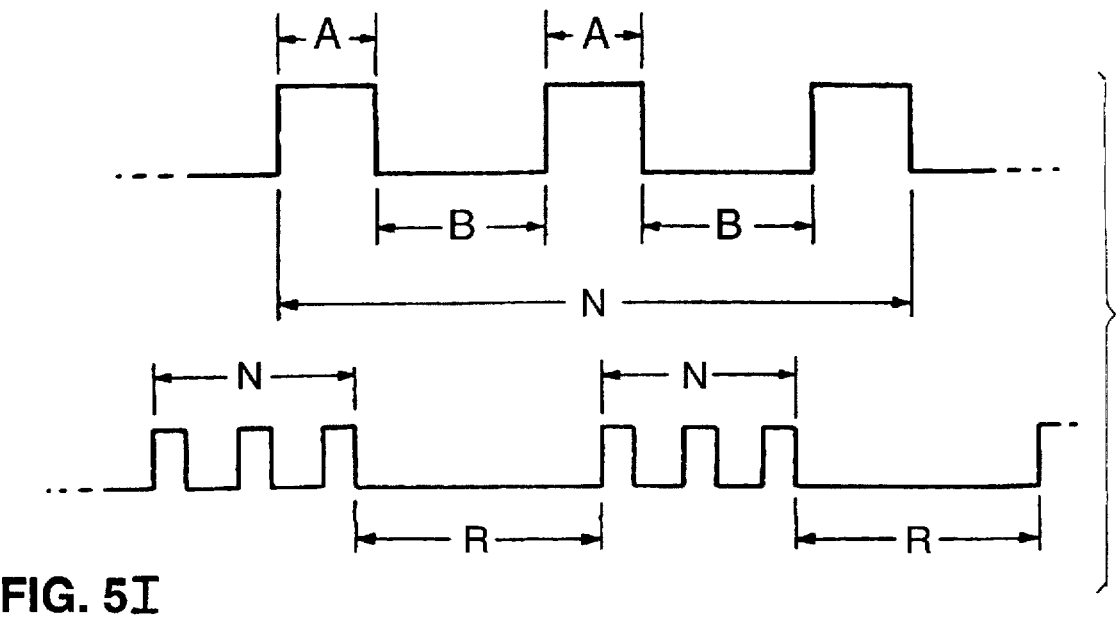

Capture of the monitor image may be performed in several different ways. The image capture following the flush may simply occur at a fixed time interval, as shown in the irrigation cycle sequence provided in FIGS. 5E-F. FIGS. 5E-F show an irrigation cycle N that includes three irrigation pulses per cycle. Each irrigation pulse is of duration A, followed by an irrigation-interrupted period B. R designates the "rest" time between cycles. An updated image is "frozen" on each falling edge of the "A" irrigation pulse. Alternatively, the image capture may be triggered by the computer controls. For example, a densitometer may be used to detect the presence of a clear optical field. The clear field may also be determined by examining the maximal image contrast obtained during the irrigation cycle, and capturing the image when the image contrast just starts to decrease from its optimal degree.

Alternatively, as stated above, control of the irrigation cycle may be performed by the operator via the foot pedal switch which activates both the flush and image capture functions. A single depression of the pedal followed by its release may correspond to a single irrigation. Continued depression of the foot pedal may then result in a repeated irrigation cycle at specified time intervals; for example, at one second internals. This allows angioscope advancement at a rate of 1.5 cm per second, with visualization of the entire length of the artery, while allowing normal blood flow to occur during the flush interrupted cycles.

Further information regarding the angioscopy imaging system described above may be obtained by reference to U.S. patent application Ser. No. 328,760, which is commonly-assigned herewith, and in which the Issue Fee was paid on Dec. 17, 1990. U.S. patent application Ser. No. 328,760 is hereby incorporated by reference.

Figure 9:
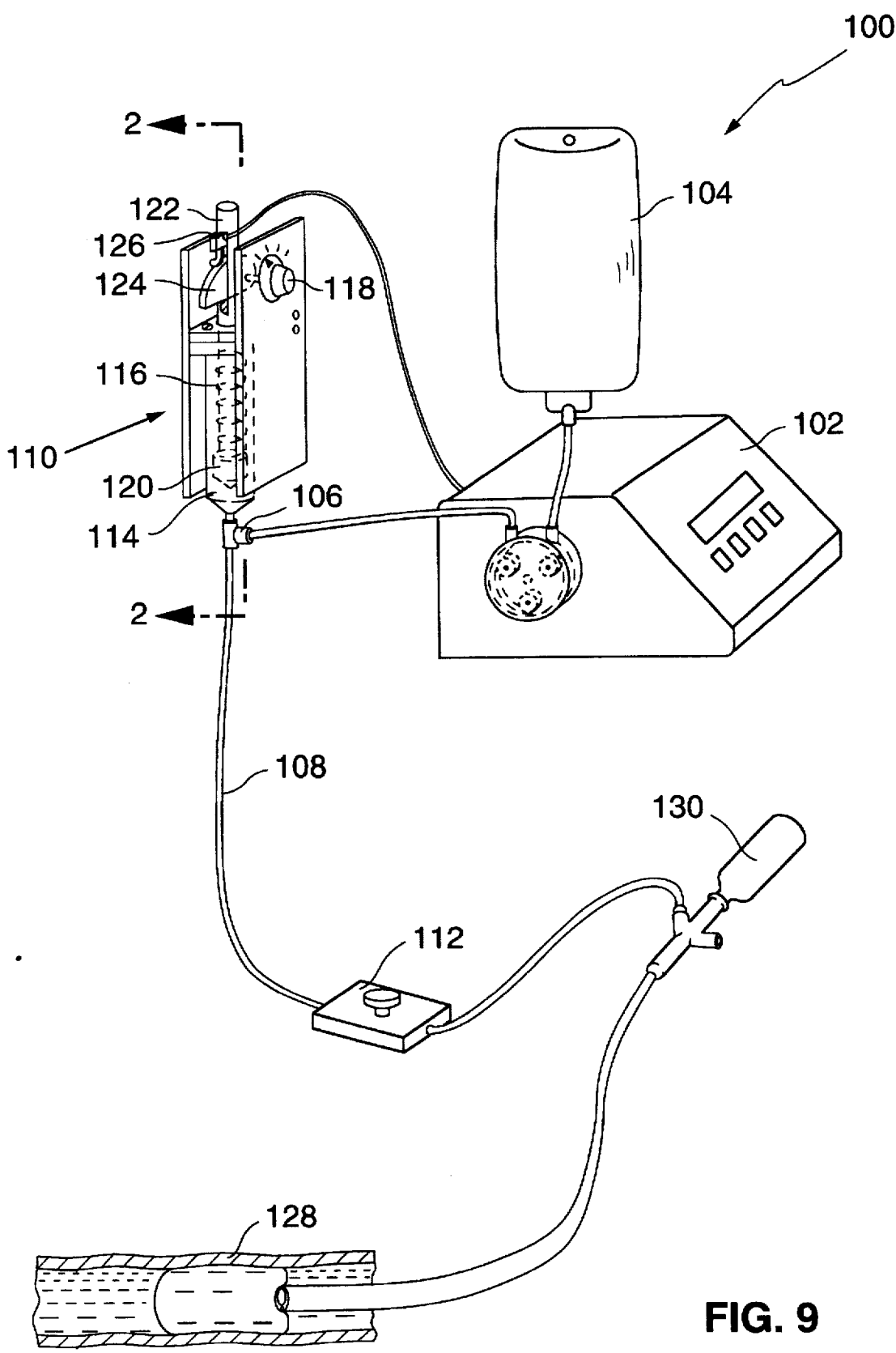
FIG. 9 is a pictorial view illustrating an alternative embodiment of an irrigation accumulator system in accordance with the present invention.

An alternative embodiment of a pressure-based irrigation accumulator system in accordance with the present invention is shown in FIG. 9.

FIG. 9 shows a roller pump irrigation accumulator system 100 that includes a conventional roller pump 102 (such as a Masterflex pump available from Cole-Parmer Instrument Co., Chicago, Ill.) that delivers saline solution from a saline reservoir 104 to a T-connection 106 in the outlet line 108 of a hypodermic syringe system 110. The outlet line 108 is clamped by a normally closed hand or foot controlled actuating valve 112. (Those skilled in the art will appreciate that the actuating valve can be readily adapted for control by the computer system described above.)

The roller pump 102 is normally on to deliver saline solution to the outlet line 108. Since the outline line 108 is clamped shut by the actuating valve, pressure builds in the line 108 and the cylinder 114 of the hypodermic syringe system 110 begins to fill. The cylinder 114 is equipped with a spring mechanism 116 (or, alternatively, with an air spring mechanism) that allows pressure to build in the cylinder 114 until it reaches a preselected pressure limit determined by the setting of a pressure control switch 118. That is, as the fluid pressure in the cylinder 114 forces a plug 120 in the cylinder, spring 116 contracts. A rod 122 connected to the plug 120 causes a cam 124 to rotate until the preset pressure is reached. At that point, the cam 124 activates a switch 126 which turns the roller pump 102 off.

With the syringe system 110 thus loaded with a defined volume of saline irrigation solution, the actuator valve 112 may be opened to deliver a controlled pulse of saline irrigation solution to the interior of a vessel 128 through angioscope 130 in the manner described above. Since delivery of the pulse reduces the pressure in the cylinder 114, the rod 122 moves toward the outlet of the cylinder 114, re-engaging the switch 126. With switch 126 re-engaged, roller pump 102 turns on to re-fill the cylinder 114 to the preset pressure.

Figure 10:
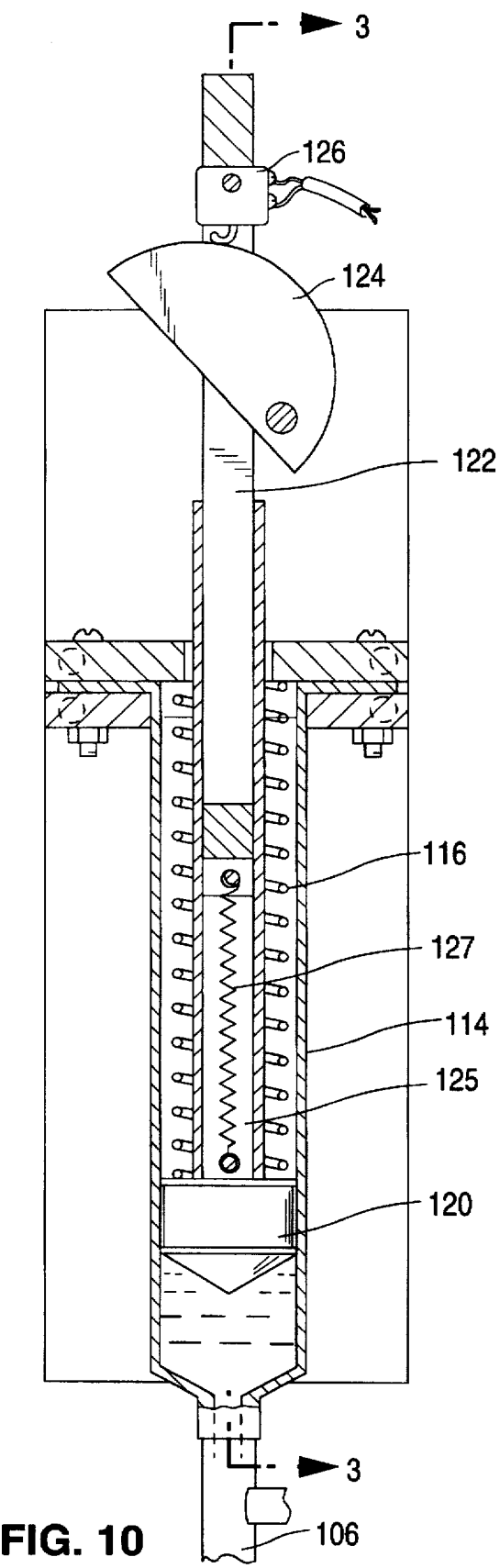
FIG. 10 is a cross-sectional view of the FIG. 9 irrigation accumulator system taken along line 2—2 in FIG. 9.
Figure 11:
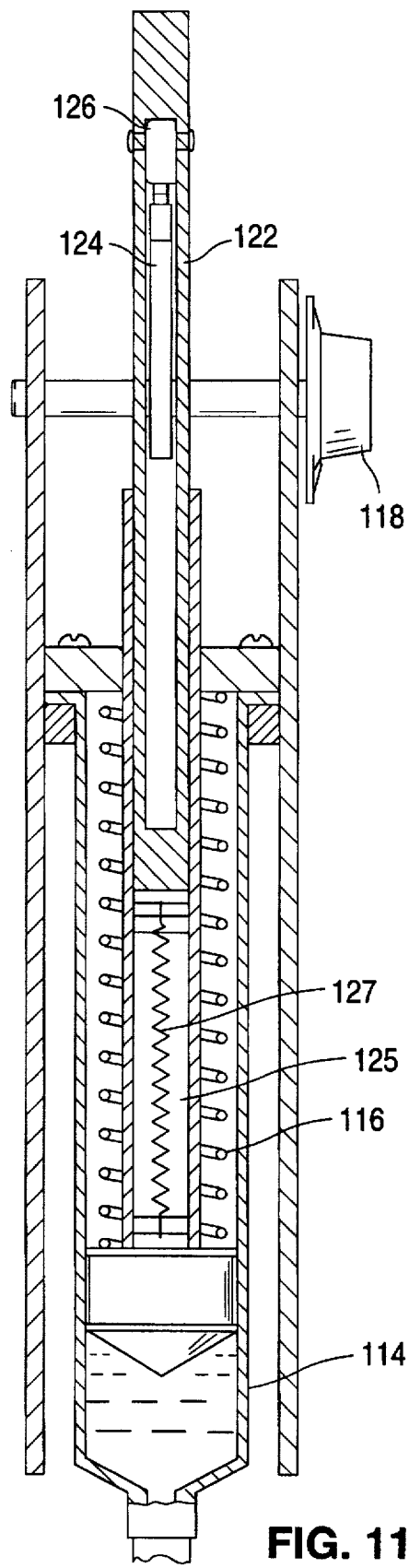
FIG. 11 is a cross-sectional view of the FIG. 9 irrigation accumulator system taken along line 3—3 in FIG. 10.

FIG. 10 shows the front view of the spring pressurized syringe 110. FIG. 11 shows the side view of the spring pressurized syringe 110. When the plunger assembly consisting of plug 120 and rod 122 of FIG. 10 is in the lower, syringe chamber empty position, and cam 124 is in the "off" position, switch 126 is open. With the switch in the open position the power to the roller pump 102 is off. When control knob 118 of FIG. 11 is rotated towards the "on" direction, cam 124 of FIG. 10 closes switch 126. This activates the roller pump 102. Cam 124 extends rod 122 to a preset distance by extending spring 127. The preset distance correlates to the amount spring 116 will be compressed which is dependent on the amount of fluid/pressure in the syringe chamber. The pressure in the syringe chamber compresses spring 116 until row 122 bottoms out in rod housing 125 opening switch 126. This deactivates the roller pump 102. This feedback loop allows a flow pump to be operated as a constant pressure pump while also allowing pressure to be preset.

Figure 12:
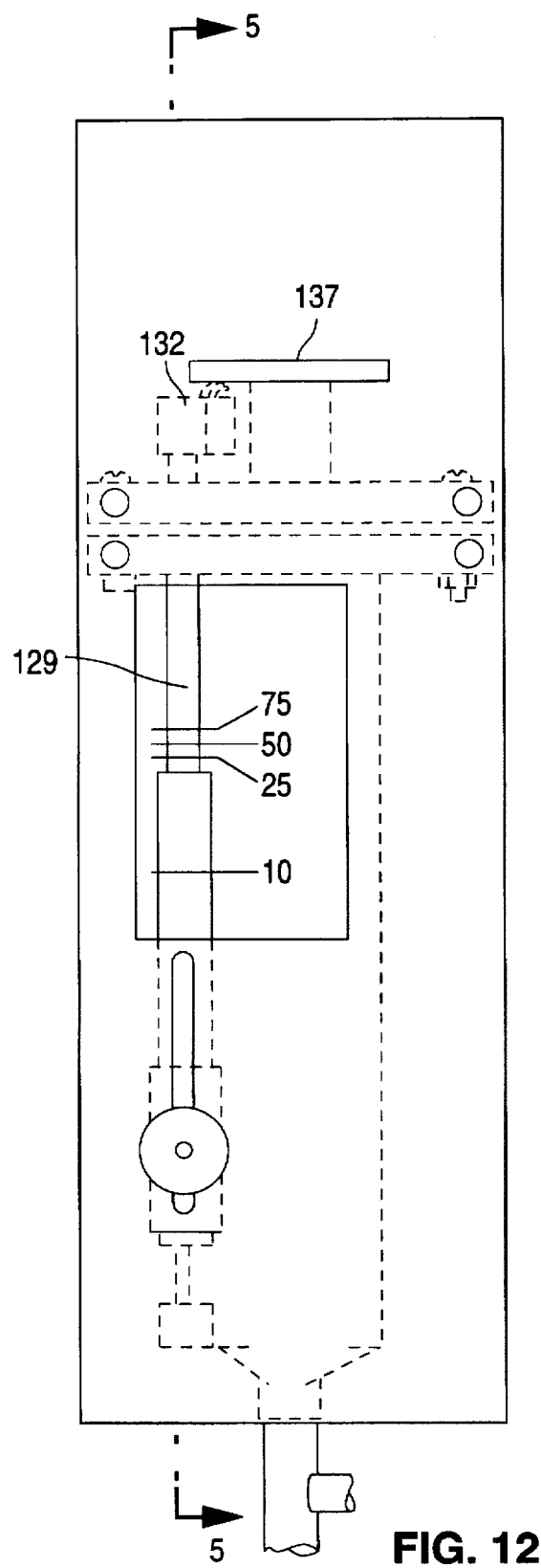
FIG. 12 is a front view of the FIG. 9 irrigation accumulator system.
Figure 13:
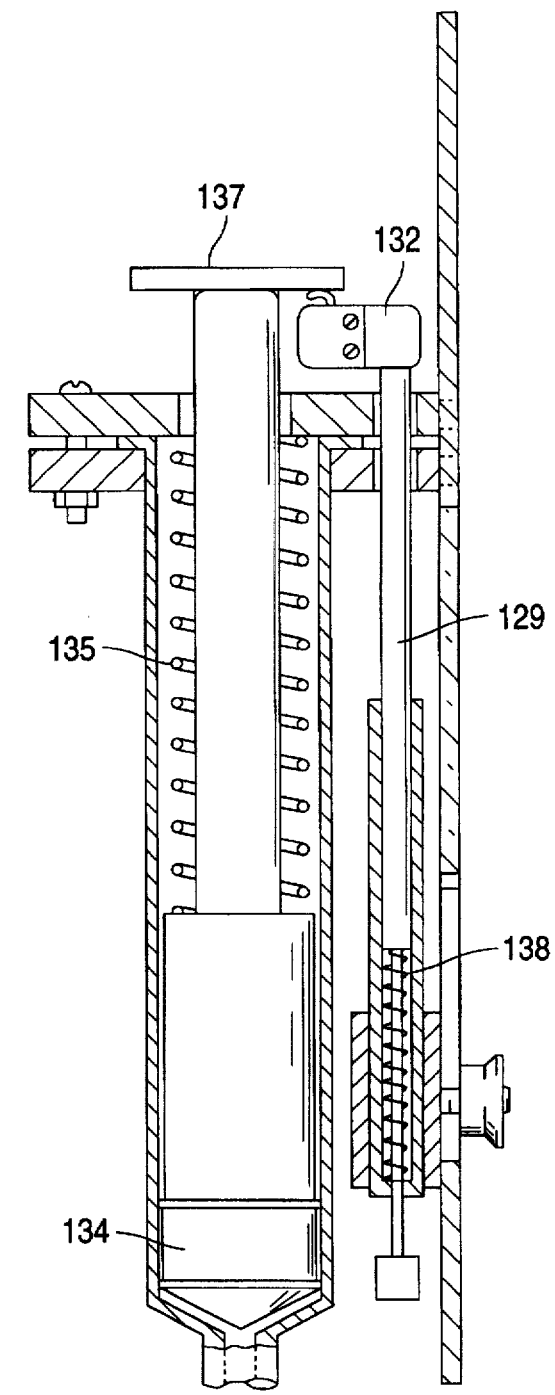
FIG. 13 is a cross-sectional view of the FIG. 9 irrigation accumulator system taken along line 5—5 in FIG. 11.

FIGS. 12 and 13 shows an alternate control mechanism for the roller pump 102. According to this alternative, when the roller pump 102 is activated by switch 132, fluid is pumped into syringe chamber. This moves plug 134, plunger 138 and platform 137 away from the switch 132. Spring 135 allows rod 129 and switch 132 to follow platform 137 until the preset distance and corresponding pressures are reached. When the preset pressures are reached, platform 137 no longer makes contact with switch 132. This deactivates the roller pump 102. When the fluid foot switch 112 (FIG. 9) is activated, the fluid escaping from the syringe allows the platform 137 to move towards and contact switch 132, thereby reactivating the roller pump 102. Thus, the plunger rod 129 and switch 132 work as a control system with a feedback loop to maintain a desired pressure within the syringe system.

It should be understood that various alternative to the embodiment of the invention described herein may be employed in practicing the invention. It is intended that the following claims define the scope of the invention and that structures and methods within the scope of these claims and their equivalents be covered thereby.

What is claimed is:

1. A pressure-based irrigation accumulator system utilizable in an angioscopy imaging system, the irrigation accumulator system comprising:

(a) reservoir means for storing irrigation solution under constant pressure;

(b) pressure means for maintaining the reservoir means at the constant pressure;

(c) delivery means for delivering irrigation solution from the reservoir means to a destination; and (d) control means for controlling the delivery means to deliver a pulse of solution at a predetermined pressure to the destination.

2. A pressure-based irrigation accumulator system utilizable in an angioscopy imaging system, the irrigation accumulator system comprising:

(a) a reservoir that holds irrigation fluid at a constant preselected pressure;

(b) pressure regulator means connected to the reservoir for maintaining the irrigation fluid at the constant preselected pressure; and (c) actuating means connected to the reservoir for controlling the flow of irrigation fluid from the reservoir to a destination, wherein the actuating means causes a pulse of fluid at the constant preselected pressure to be delivered to the destination.

3. A pressure-based irrigation accumulator system utilizable in an angioscopy imaging system, the irrigation accumulator system comprising:

(a) a reservoir that holds irrigation fluid;

(b) irrigation fluid supply means responsive to a control signal for delivering a pulse of irrigation fluid at a preselected pressure to a supply line connected to the irrigation fluid supply means;

(c) pressure sensitive irrigation fluid delivery means connected to receive the pulse of irrigation fluid from the supply line and including pressure sensitive means for providing the control signal to the irrigation fluid supply means to maintain the pressure of the irrigation fluid in the irrigation fluid delivery means at the preselected pressure; and (d) actuating means connected to the irrigation fluid delivery means for controlling the flow of the pulse of irrigation fluid from the irrigation fluid delivery means to a destination.

4. A fluid delivery system for providing irrigation fluid to an angioscopy imaging system, comprising:

a reservoir of irrigation solution;

a pump to deliver irrigation solution from the reservoir to a fluid delivery means;

fluid delivery means for delivering the irrigation fluid to the imaging system, wherein the fluid delivery means includes control means for operating the pump and producing a predetermined fluid pressure within the fluid delivery means; and actuating means to control the flow of fluid from the fluid delivery means to the imaging system, wherein the actuating means operates to deliver a pulse of fluid at the predetermined pressure to the imaging system.

5. The fluid delivery system of claim 4, wherein, the irrigation fluid is a saline solution.

6. The fluid delivery system of claim 4, wherein, the pump is a roller pump.

* * * * *